United States Patent [19]

German et al.

[11] Patent Number: 5,456,912
[45] Date of Patent: Oct. 10, 1995

[54] NON-METHYLENE INTERRUPTED FATTY ACIDS AS IMMUNOMODULATORS

[75] Inventors: J. Bruce German; M. Eric Gershwin, both of Davis, Calif.; Alvin Berger, Arlington, Va.

[73] Assignee: The Regents of the University of California, Oakland, Calif.

[21] Appl. No.: 174,956

[22] Filed: Dec. 28, 1993

[51] Int. Cl.$^6$ .......................... A61K 31/19; A61K 35/78
[52] U.S. Cl. ...................... 424/195.1; 514/814; 514/825; 514/859; 514/861; 514/863; 514/864; 514/866; 514/885; 514/886
[58] Field of Search .................................. 514/825, 814, 514/866, 859, 861, 863, 864, 885, 886; 424/195.1

[56] References Cited

U.S. PATENT DOCUMENTS

| | | | |
|---|---|---|---|
| 4,181,670 | 1/1980 | Liang | 424/312 |
| 4,515,727 | 5/1985 | Patterson et al. | 260/413 |
| 4,560,514 | 12/1985 | Samuelsson et al. | 260/404 |
| 4,761,425 | 8/1988 | Girard et al. | 514/456 |
| 5,178,873 | 1/1993 | Horrobin et al. | 424/422 |
| 5,202,313 | 4/1993 | Bombardelli et al. | 514/100 |

OTHER PUBLICATIONS

Joklik et al, Zinsser Microbiology 20th edition, 1992, pp. 323–344, published by Appleton & Lange, Norwalk, Conn., USA.
G. Fernandes, et al. Modulation of Gene Expression in Autoimmune Disease and Aging by Food Restriction and Dietary Lipids (42983). Proceedings of the Society for Experimental Biology and Medicine, vol. 193, 1990, pp. 16–22.
Brian L. Kotzin, et al. Genetic contributions to Lupus–Like Disease in NZB/NZW Mice. The American Journal of Medicine, vol. 85 (suppl 6A), Dec. 23, 1988, pp. 29–31.
Belur R. Lokesh, et al. Docosahexaenoic Acid and Other Dietary Polyunsaturated Fatty Acids Suppress Leukotriene Synthesis by Mouse Peritoneal Macrophages. Lipids, vol. 23, No. 10, 1988, pp. 968–972.
Vicki E. Kelley, et al. Increased Renal Thromboxane Production in Murine Lupus Nephritis. Journal of Clinical Investigations, vol. 77, Jan. 1986, pp. 252–259.
Vicki E. Kelley, et al. Enriched Lipid Diet Accelerates Lupus Nephritis in NZBxW Mice. American Journal of Pathology, vol. 111, No. 3, 1983, pp. 288–297.
D. R. Robinson, et al. Alleviation of Murine Autoimmune Disease by Dietary marine Lipids. Advances in Prostaglandin, Thromboxane, and Leukotriene Research, vol. 17, 1987, pp. 850–853.
James D. Prickett, et al. Effects of Dietary Enrichment With Eicosapentaenoic Acid Upon Autoimmune Nephritis in Female NZBxNZW/F$_1$ Mice. Arthritis and Rheumatism, vol. 26, No. 2, Feb. 1983, pp. 133–139.

Nancy J. Alexander, et al. The Type of Dietary Fat Affects the Severity of Autoimmune Disease in NZB/NZW Mice. American Journal of Pathology, vol. 127, 1987, pp. 106–121.
W. John W. Morrow, et al. Dietary Fat and Immune Function. I. Antibody Responses, Lymphocyte and Accessory Cell Function in (NZB x NZW) F$_1$ Mice. Journal of Immunology, vol. 135, No. 6, Dec. 1985, pp. 3857–3863.
Norman Talal, et al. The Pathogenesis of Autoimmunity in New Zealand Black Mice. Current Topics in Microbiology and Immunology, vol. 64, 1974, pp. 79–103.
Berger, A., et al., "Incorporation of dietary 5,11, 14–icosatrienoate into various mouse phospholipid classes and tissues," *J. Nutr. Biochem.*, vol. 4, pp. 409–420 (Jul. 1993).
Keen, C. L., et al., "Nutritional Modulation of Murine Models of Autoimmunity," *Rheumatic Disease Clinics of North America*, vol. 17, No. 2, pp. 223–234 (May 1991).
Berger, A., and German J. B., "Extensive incorporation of dietary Δ–5,11,14 eicosatrienoate into the phosphatidylinositol pool," *Biochimica et Biophysica Acta*, vol. 1085, pp. 371–376 (1991).
Chiang, B.–L., et al., "The BM12 Mutation and Autoantibodies to dsDNA in NZB.H–2$^{bm12}$ Mice," *The Journal of Immunology*, vol. 145, No. 1, pp. 94–101 (1 Jul. 1990).
German, J. B., et al., "The Effect of Dietary Fish Oils on Eicosanoid Biosynthesis in Peritoneal Macrophages is Influenced by Both Dietary N–6 Polyunsaturated Fats and Total Dietary Fat," *Prostaglandins Luekotrienes and Essential Fatty Acids*, pp. 37–45 (Longman Group UK Ltd 1988).
Lokesh, B. R., "Docosahexaenoic Acid and Other Dietary Polyunsaturated Fatty Acids Suppress Leukotriene Synthesis by Mouse Peritoneal Macrophages," *Lipids*, vol. 23, No. 19 (1988) pp. 968–973.
German, J. B., "Modulation of Zymosan Stimulated Leukotriene Release by Dietary Unsaturated Fatty Acids," *Prostaglandins, Leukotrienes and Medicine*, vol. 30, pp. 69–76 (1987).
Kanner, J., et al., "Initiation of Lipid Peroxidation in Biological Systems," *CRC Critical Reviews in Food Science and Nutrition*, vol. 25, Iss. 4 (1987) pp. 317–364.
Beach, R. S., "Nutrial Factors and Autoimmunity: I. Immunopathology of Zinc Deprivation in New Zealand Mice," *The Journal of Immunology*, vol. 126, No. 5 (May 1981) pp. 1999–2006.

*Primary Examiner*—Ronald W. Griffin
*Attorney, Agent, or Firm*—Townsend and Townsend Khourie and Crew

[57] ABSTRACT

Autoimmune diseases are controlled by the administration of non-methylene interrupted fatty acids of the formula

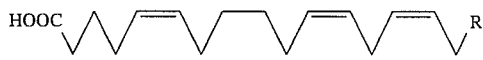

in which R is alkyl or alkenyl. A preferred compound within the scope of this formula is 5,11,14-eicosatrienoic acid.

6 Claims, 3 Drawing Sheets

NON-METHYLENE INTERRUPTED FATTY ACIDS AS IMMUNOMODULATORS

This invention was made with United States Government support, under an ILSI Nutrition Foundation Award and NIH Grant CA 20816. The Government accordingly has certain rights in this invention.

BACKGROUND OF THE INVENTION

Autoimmune diseases are widespread and have been the subject of considerable attention in attempts to develop an understanding of the diseases themselves and in attempts to develop therapies. The most common approach to treating autoimmune diseases and other immunopathologies is general immunosuppression. Immunosuppression has the obvious disadvantage of crippling the ability of the subject to respond to materials which are truly foreign and against which an immune response is truly needed. A slightly more sophisticated approach relies on the removal of antibodies or immune complexes involving the target tissue. This approach is difficult to accomplish, however, and has adverse side effects as well.

Investigations of further approaches have included studies related to the role of cell membranes. Polyunsaturated fatty acids in cell membranes, for example, are known to be critical to the immune function. Polyunsaturated fatty acids of particular interest are the eicosanoids, which are the metabolites of arachidonic acid (5,8, 11,14-eicosatetraenoic acid, referred to variously herein as 20:4(5,8,11,14) and 20:4(n-6)). Eicosanoids modulate the immune system either directly by stimulating target cells or indirectly by modulating the production of other soluble regulatory factors such as tumor necrosis factor and cytokines.

There have been attempts to control autoimmunity by substituting other fatty acids for arachidonic acid. The substitutes have primarily been fatty acids of the n-3 type, such as γ-linolenic acid (9,12,15-octadecatrienoic acid, or 18:3(9,12,15)) and fish oils, which are a source of n-3 fatty acids. Unfortunately, these are efficacious only at very high levels, and compete poorly with the arachidonic acid which is otherwise present in human diets. Furthermore, these substitutes are particularly ineffective in replacing the eicosanoid content of the phosphatidyl inositols, which are a critical class of lipids. As a result, this approach has not met with success, and no useful data confirming its viability has been reported.

SUMMARY OF THE INVENTION

It has now been discovered that the formation of autoantibodies, and hence the onset of autoimmune diseases, can be suppressed by the use of compounds of the formula

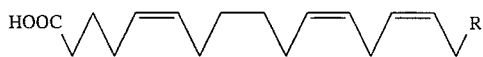

where R is $C_1$–$C_{10}$ alkyl, $C_2$–$C_{10}$ alk-1-enyl, $C_2$–$C_{10}$ alka-1,4-dienyl, or $C_2$–$C_{10}$ alka-1,4,7-trienyl. Preferred compounds are those in which R is $C_1$–$C_6$ alkyl or $C_2$–$C_6$ alk-1-en particularly preferred are those in which R is n-butyl (5,11,14-eicosatrienoic acid) or 1- n-butenyl (5,11, 14,17-eicosatetraenoic acid), and the most preferred is that in which R is n-butyl (5,11,14-eicosatrienoic acid).

DETAILED DESCRIPTION OF THE INVENTION AND PREFERRED EMBODIMENTS

Figure 1:
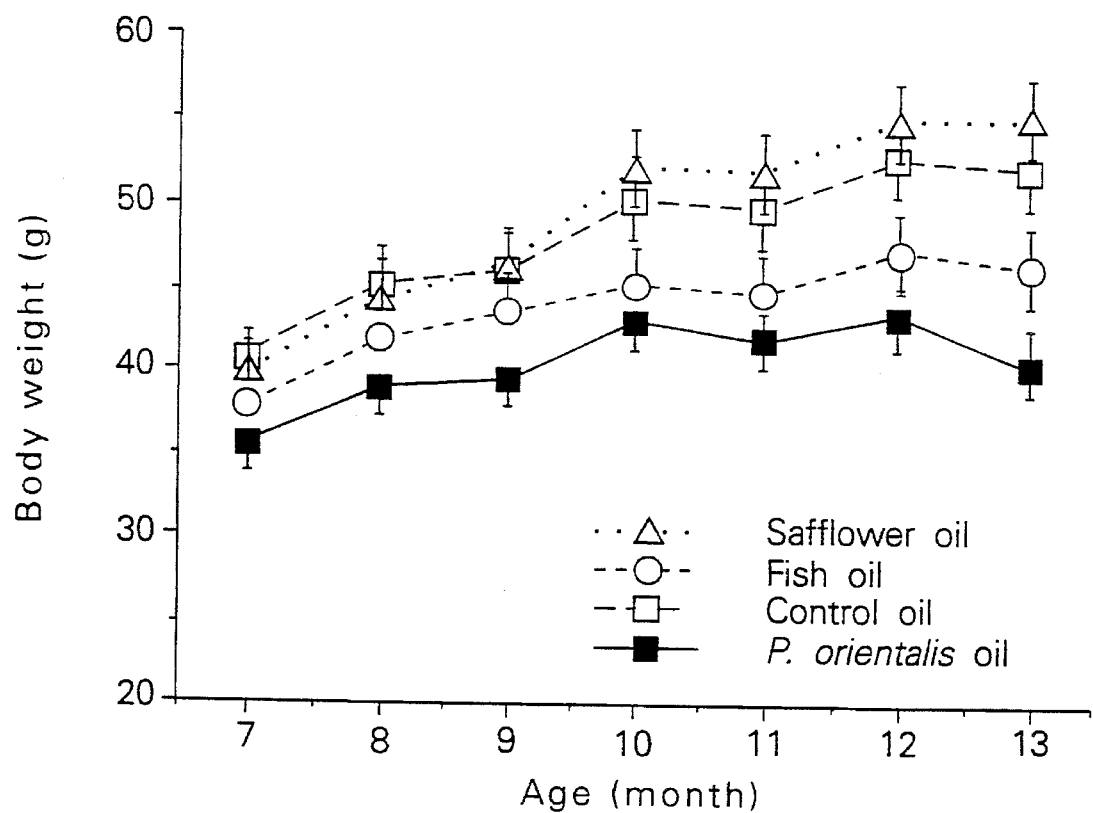
FIG. 1 is a representation of experimental results in which changes in body weight are correlated to the presence of NMIFA's in the diet.

The fatty acids which are the subject of this invention are polyunsaturated fatty acids which are linear and monocarboxylic, with all double bonds being cis-double bonds. The acids are variants on methylene-interrupted structures.

Several types of nomenclature are used in this specification, and these are as follows.

(a) Nomenclature for individual compounds indicating number of carbon atoms and number and position of double bonds, typified by "20:4(5,8,11,14)" for arachidonic acid: the number preceding the colon is the total number of carbon atoms, the number immediately following the colon is the number of double bonds, and the numbers in parentheses are the positions of the double bonds, starting from the end of the chain bearing the carboxylic acid group. In all compounds referred to in this manner, except where otherwise indicated, all double bonds are cis.

(b) Nomenclature for classes of compounds indicating the location of the double bond furthest from the carboxylic acid group, typified by "n-3" or "n-6": the number following the dash denotes the position of the double bond closest to the methyl end of the molecule, counting from the methyl end. Thus, arachidonic acid is in the n-6 class, as is 5,11,14-eicosatrienoic acid (20:3(5,11,14)), whereas 5,11,14,17-eicosatetraenoic acid (20:4(5,11,14,17)) is in the n-3 class. This nomenclature is equivalent to "ω-" nomenclature in the literature, "ω" and "n" being interchangeable.

(c) "NMIFA": acronym for non-methylene-interrupted fatty acid, referring to a fatty acid with a series of double bonds in which at least one adjacent pair of double bonds is separated by at least two carbon atoms, i.e., by a group other than a single methylene group.

The fatty acids of this invention (i.e., the NMIFA's of the invention) are naturally-occurring substances which generally occur as one fatty acid in a mixture of fatty acids. The NMIFA's are found in a wide variety of plants as minor fractions of the total fatty acid composition. Both the extraction of the fatty acid mixtures from their natural sources and the extraction of the desired NMIFA's from the remaining fatty acids can be achieved by conventional extraction and purification procedures well known among those skilled in the art. Alternatively, the NMIFA's can be administered as part of the mixture of fatty acids in which they are found in the plant source. Surprisingly, the NMIFA's are highly competitive with other fatty acids for acylation into cell membranes as a replacement or substitute for arachidonic acid.

The natural sources of fatty acids containing NMIFA's are primarily plant seeds, and prominent among these are exotic conifers and ornamental shrubs. The seed oils from these plants are similar to normal edible oils, containing largely oleic, linoleic and linolenic acids, but also containing useful amounts of the NMIFA's. Table I lists examples of seeds whose lipid contents contain significant amounts of either or both of the two NMIFA's 20:3(5,11,14) and 20:4(5,11,14,17). The symbol "..." denotes the NMIFA's.

TABLE I

Fatty Acid Composition of Selected Seed Oils

| | Percent Fatty Acid in Oil Oil Source: | | |
|---|---|---|---|
| Fatty Acid | Juniperis virginiensis | Platycladus orientalis | Juniperis chinensis |
| 16:0 | 4.0 | 6.1 | 6.0 |
| 18:0 | 3.4 | 3.9 | 4.2 |
| 18:1 n-9 | 12.3 | 11.3 | 13.5 |
| 18:2 n-6 | 30.2 | 24.0 | 33.1 |
| 18:3 n-3 | 20.1 | 40.7 | 18.0 |
| 20:1 n-9 | 1.0 | 0.7 | 1.0 |
| 20:2 n-6 | 1.8 | 0 | 1.0 |
| 20:3(5,11,14) | 14.8 | 2.9 | 12.3 |
| 20:4(5,11,14,17) | 6.5 | 9.1 | 7.4 |

Table II below lists additional plant seeds containing the two NMIFA's shown in Table I plus others.

TABLE II

Contents of NMIFA Fraction of Fatty Acids in Selected Seeds

| | | Percent of Total Fatty Acids NMIFA: | | | | |
|---|---|---|---|---|---|---|
| Source Seed | Total Fats (%) | 18:2 (5,11) | 20:2 (5,11) | 18:3 (5t,9,12)* | 20:3 (5,11,14) | 20:4 (5,11,14,17) |
| Gingko biloba | 1.8 | 1.8 | 0 | 0 | 4.4 | 0 |
| Athrotaxis cuppressoides | 4.6 | 0 | 0 | 0 | 3.5 | 4.0 |
| Podocarpus macrophylla | 9.2 | 0 | 0 | 29.5 | 3.8 | 1.2 |
| Platycladus pyramidalis | 35 | 0 | 1 | 0 | 2.8 | 7.3 |
| Platycladus compacta | 33 | 0 | 0 | 0 | 3.1 | 8.0 |
| Ephedra intermedia | n.d. | 0 | 0 | 0 | 5.6 | 16.0 |
| Sciadopitys verticalla | 37 | 0 | 0 | 0 | 15.0 | 0 |
| Juniperis virginiensis | 30 | 0 | 0.8 | 0 | 14.8 | 6.5 |

*Note: "t" denotes a trans-double bond

Administration of the NMIFA's of the present invention may be achieved by known methods. The compounds can be administered, for example, as a food material, or as a replacement for the oils normally used in food formulations or recipes, or as part of a mixture of oils used in this manner. The compounds can also be administered as part of a nutritional supplement, such as tablets or capsules taken orally on a daily basis. Binders, matrices, and other conventional adjuvants normally found in supplements of these types will generally be included here as well. Typical dosages for such methods may vary widely, but will most often fall within the range of about 2 mg per kg of body weight to about 2000 mg per kg, and more often within the range of about 5 to about 500 mg per kg.

Administration can also be achieved by enteral infusion, either as lipid emulsions or by liposomal infusion. Liposomes are dual character molecules (polar:nonpolar) which exist as aggregates in aqueous solution. These molecules include one or more various types of substances including nonpolar lipids, polar lipids, mono- and diglycerides, sulfatides, lysolecithin, phospholipids, saponin, bile acids and salts. Liposomes can exist as emulsions and foams, micelies, insoluble monolayers, liquid crystals, phospholipid dispersions or lamellar layers. The NMIFA can be incorporated in the liposome, optionally in conjunction with an appropriate ligand or mimetic which binds to specific cell receptors.

Liposomes are generally formed from standard vesicle-forming lipids, which generally include neutral and negatively charged phospholipids and a sterol, such as cholesterol. The selection of lipids is generally guided by consideration of various factors, such as for example the desired liposome size and the need for stability of the liposomes in the bloodstream. Typically, the major lipid component in the liposomes is phosphatidylcholine. Partially hydrogenated egg phosphatidylcholine is a typical example.

The charge on the liposome is an important determinant in the clearance of the liposome from the blood. Negatively charged liposomes are taken up rapidly by the reticuloendothelial system and thus have relatively short half-lives in the bloodstream. For certain applications, on the other hand, longer half-lives may be desirable. These applications may involve a sustained release or the facilitation of the targeting of the NMIFA's to a desired site before being removed by the reticuloendothelial system.

Liposomes typically contain about 5–15 mole percent negatively charged phospholipids, such as phosphatidylglycerol, phosphatidylserine or phosphatidylinositol. Negatively charged phospholipids help prevent spontaneous aggregation of the liposomes and thus lower the incidence of aggregates formed from undersized liposomes. Membrane-rigidifying agents, such as sphingomyelin or a saturated neutral phospholipid, at a concentration of at least about 50 mole percent, and 5–15 mole percent of monosialylganglioside, may also be included to provide increased circulation of the liposome preparation in the bloodstream.

Liposome suspensions may also include lipid-protective agents to protect the lipids from free-radical and lipid-peroxidative damage during storage. Examples of such agents are lipophilic free-radical quenchers such as alphatocopherol, and water-soluble ironspecific chelators such as ferrioxianine.

Liposomes can be prepared by a variety of methods known among those skilled in the art. The liposomes can then be sized to a desired size range and a relatively narrow size distribution. A size range which permits the liposome suspension to be sterilized by filtration through a conventional filter, for example, is about 0.2–0.4 microns.

Once prepared, the liposomes can be administered enterally, parenterally, or orally. Formulations for administration will generally comprise a solution of the compound dissolved or suspended in an acceptable vehicle, the appropriate choices of which will readily occur to those skilled in the art. The formulations may further contain pharmaceutically acceptable auxiliary substances as required to approximate physiological conditions, such as pH adjusting and buffering agents, tonicity adjusting agents, and wetting agents.

The present invention is applicable to the treatment and control of autoimmune diseases in general. Examples are rheumatoid arthritis, lupus erythmatosis, multiple sclerosis, myasthenia gravis, and approximately thirty other diseases currently known. Subjects to whom the NMIFA's of this invention may be administered are mammalian subjects, particularly humans.

The following series of examples are reports of experiments which were performed on mice to illustrate the effects of administering non-methylene-interrupted fatty acids to the mice. General procedures applicable to all examples were as follows.

The mice were three-month-old female NZB (H-$2^d$) mice, obtained from Jackson Laboratory (Bar Harbor, Me., U.S.A.) and maintained on Rodent Labratory Chow® (Purina Mills, Inc., St. Louis, Mo., U.S.A.) for two weeks prior to the start of the experiment. Food and distilled/deionized water were given to the mice ad libitum. The mice were kept in a humidity-controlled, temperature-controlled room at 25° C., with the dark cycle between 6:00 p.m. and 7:00 a.m.

At the start of each experiment, the mice were placed on test diets, which were fat-free AIN 76A diets (Dyets, Inc., Bethlehem, Pa., U.S.A.) supplemented with one of four oils at a level of 10% by weight. The four oils were as follows:

(1) Safflower oil (Dyets, Inc., Bethlehem, Pa., U.S.A.)

(2) A mixture of fish oil (NIH Biomedical Test Material L8195BB, National Institutes of Health, Bethesda, Md., U.S.A.) and safflower oil, at a weight ratio of 9:1

(3) A control oil consisting of a mixture of 15 % olive oil (G. Sensat, Extra Virgin #5, Specialty Food and Beverage Sales, West Milford, N.J., U.S.A.), 15 % safflower oil, and 70% linseed oil (Spectrum Marketing, Petaluma, Calif., U.S.A.). This control oil is referred to herein as "*P. orientalis* control oil" since it contains oleic acid [18:1(9)] in an amount very close to the total of 18:1(9), and NMIFA's, 18:2(9,12), 18:3(9,12,15) and other methylene-interrupted fatty acids at levels very close to the levels of the same fatty acids in *P. orientalis* oil. The composition of this control oil is thus essentially the same as that of *P. orientalis* oil except that the NMIFA's are replaced by 18:1(9).

(4) *P. orientalis* oil derived from seeds obtained from F.W. Schumacher Co., Inc. (Sanwich, Mass., U.S.A.). To extract the oil, the seeds were sieved, freeze-dried and ground in a hammer mill under liquid nitrogen. The oils were extracted from the seeds by treatment with hot isopropanol/chloroform, and the extract was evaporated on a rotary evaporator and redissolved in hexane, then purified by filtration, water washes and centrifugation. The solvent was finally removed by vacuum evaporation.

To minimize autoxidation and to balance antioxidant levels among the oils, *tert*-butylhydroquinone was added to each oil to a concentration of 0.2 mg per gram of oil. The safflower oil, fish oil and control oil diets were prepared in a commercial mixer in 5 kg lots, sealed under nitrogen in freezer bags in 250 g quantities and stored at -70° C. The *P. orientalis* diet was prepared weekly. The fatty acid composition of each of the four diets is shown in Table III.

TABLE III

Fatty Acid Composition of Test Oils

| Fatty Acid ("** ... **" denotes NMIFA[b]) | Fatty Acid Composition of Test Oil (mole %)[a] Test Oil: | | | |
|---|---|---|---|---|
| | Safflower | Fish + Safflower (9:1) | P. orientalis control | P. orientalis |
| 14:0 | 0.2 | 5.6 | 0.0 | 0.0 |
| 16:0 | 7.2 | 14.1 | 6.2 | 5.9 |
| 16:1(9) | 0.0 | 7.6 | 0.1 | 0.0 |
| 18:0 | 2.2 | 2.5 | 3.8 | 4.0 |

TABLE III-continued

Fatty Acid Composition of Test Oils

| Fatty Acid ("** ... **" denotes NMIFA[b]) | Fatty Acid Composition of Test Oil (mole %)[a] Test Oil: | | | |
|---|---|---|---|---|
| | Safflower | Fish + Safflower (9:1) | P. orientalis control | P. orientalis |
| 18:1(9) | 12.0 | 8.7 | 24.9 | 11.3 |
| 18:2(9,12) | 77.7 | 8.9 | 23.9 | 23.8 |
| 18:3(9,12,15) | 0.0 | 0.9 | 40.8 | 40.1 |
| 20:1(11) | 0.1 | 1.4 | 0.1 | 0.6 |
| 20:2(11,14) | 0.0 | 0.2 | 0.0 | 0.7 |
| 20:3(5,11,14) | 0.0 | 0.0 | 0.0 | 3.1 |
| 20:4(5,11,14,17) | 0.0 | 0.0 | 0.0 | 9.1 |
| 20:5(5,8,11,14,17) | 0.0 | 11.2 | 0.0 | 0.0 |
| 22:6(4,7,10,13,16,19) | 0.0 | 9.8 | 0.0 | 0.0 |
| $C_{22} + C_{24}$[c] | 0.3 | 13.4 | 0.1 | 0.0 |
| Others[d] | 0.3 | 15.7 | 0.1 | 1.4 |
| Total NMIFA's | | | 0.0 | 13.1 |
| Total NMIFA's + 18:1(9) | | | 24.9 | 24.4 |

Notes:
[a] Each value in this table is the mean of two determinations. The value "0.0" denotes a level below the detection limit, which was 0.01%.
[b] "NMIFA": Non-methylene-interrupted fatty acid.
[c] The total of all $C_{22}$ and $C_{24}$ fatty acids.
[d] "Others" include 15:0, 16:1(11), 16:2(9,12), 16:3(6,9,12), 16:4(6,9,12,15), 18:1(11), 18:4(6,9,12,15), 20:0, 20:2(5,11), 20:3(11,14,17), and 20:4(8,11,14,17).

Fifty-six female mice were randomly placed in each of four groups, with one of the four diets being fed to each group. Feeding was continued until the mice were 13 months of age. Food was given ad libitum in ceramic feed cups daily, and uneaten food was discarded. Deionized water was provided by a pressure-sensitive nozzle. Feed cups, cages and bedding were cleaned every 2 to 4 days as needed.

EXAMPLE 1

Body Weight Study

The mice in each of the dietary groups described above were individually weighed on a weekly basis during administration of the test diets. Prior to the start of the study, there was no significant difference between the groups in terms of the average body weights. Monthly values of the weights obtained during the test diet period are shown in FIG. 1, which is a plot of the mean values (with the standard error following the ± sign) of the body weight for each group beginning at seven months of age. The triangles represent the group with the safflower oil diet; the circles represent the group with the fish/safflower oil diet; the open squares represent the group with the *P. orientalis* control oil diet; and the filled squares represent the group with the *P. orientalis* diet.

Statistically significant differences, as determined by $p<0.05$ according to Fisher's Protected Least Significant Difference (Daly, L.E., et al., *Interpretation and Uses of Medical Statistics*, Blackwell Scientific, Oxford, 00. 139–156, 1991), were noted as follows:

8 months: *P. orientalis* oil vs. *P. orientalis* control oil 9 months: *P. orientalis* oil vs. *P. orientalis* control and safflower oils 10 months: *P. orientalis* oil vs. *P. orientalis* control and safflower oils 11 months: *P. orientalis* oil vs. *P. orientalis* control and safflower oils, fish/safflower oil vs. safflower oil 12 months: *P. orientalis* oil vs. *P. orientalis* control and safflower oils 13 months: *P. orientalis* oil vs. *P. orientalis* control and safflower oils, fish/safflower oil vs. safflower oil

EXAMPLE 2

Study of Incorporation of NMIFA's Into Serum Lipids

The mice were bled monthly by retro-orbital bleeding. Serum samples from the bleeds were acidified with 0.5 M acetic acid (pH 4.0) and extracted by the Folch method (Folch, et al., *I. Biol. Chem.* 226:497–509 (1957)). Phospholipids and cholesterol esters were separated by high performance thin layer chromatography (HPTLC) using pre-coated silica gel 60 plates (E. Merck, Darmstadt, Germany) and a solvent system of petroleum ether/ethyl ether/acetic acid (80/20/1, volume basis). The solutes were visualized by spraying the plates with 8-hydroxyl-1,3,6-pyrenetrisulfonic acid trisodium salt (20 mg/100 mL methanol) and viewing under ultraviolet light. Lipid classes were identified as either phospholipids or cholesterol esters by comparison against industry available standards (Sigma Chemical Co., St. Louis, Mo., U.S.A.).

The lipids were then removed from the HPTLC plates and the acyl groups were quantitatively converted to fatty acid methyl esters by heating to 100° C. in methanol for 1 hour with acetyl chloride as an acid catalyst. The fatty acid methyl esters were separated and quantified by capillary gas liquid chromatography (GLC) using a Hewlett Packard Gas Chromatograph (Model 5890A) equipped with a DB-23 capillary column (25 m ×0.25 mm i.d., stationary phase 50% cyanopropyl silicone, film thickness 0.25 μm; J&W Scientific, Folsom, Calif., U.S.A.), a flame ionization detector and a 3392 A integrator. The GLC conditions were as follows:

initial oven temperature: 170° C.

final oven temperature: 210° C.

rate of change: 5° C./min initial column hold time: 1 minute final column hold time: 5 minutes injector temperature: 250° C.

detector temperature: 280° C.

The fatty acid methyl esters, with heptadecanoic acid methyl ester as an internal standard, were identified by comparison of retention times to authentic standards (NuChek Prep, Elysian, Minn., U.S.A.).

The results of these analyses for fatty acids in serum are shown in Table IV (for phospholipids) and Table V (for cholesterol esters).

TABLE IV

Test Results on 8-Month-Old NZB Mice
Fatty Acid Content of Total Serum Phospholipids vs. Diet

| Fatty Acid ("** ... **" denotes NMIFA[b]) | Percents of Fatty Acids Detected in Serum Phospholipids (mole %)[a] Test Oil in Diet: | | | |
|---|---|---|---|---|
| | Safflower | Fish + Safflower (9:1) | *P. orientalis* control | *P. orientalis* |
| 16:0 | 21.0 ± 0.7 | 31.3 ± 1.6[c] | 22.5 ± 0.7 | 21.3 ± 0.7 |
| 18:0 | 26.9 ± 1.0 | 26.1 ± 1.0 | 23.4 ± 1.5 | 25.4 ± 1.6 |
| 18:1(9) + (11) | 7.1 ± 0.5 | 8.8 ± 0.6 | 9.9 ± 0.7[d] | 7.5 ± 0.2 |
| 18:2(9,12) | 23.6 ± 1.1[e] | 9.3 ± 0.3[e] | 21.4 ± 1.6 | 17.1 ± 0.3 |
| 18:3(6,9,12) | 0.3 ± 0.1 | 0.4 ± 0.1 | 0.3 ± 0.1 | 0.4 ± 0.1 |
| 18:3(9,12,15) | 0.0 ± 0.0 | 0.0 ± 0.0[f] | 1.2 ± 0.3 | 1.3 ± 0.1 |
| 20:3(5,11,14) | 0.0 ± 0.0 | 0.0 ± 0.0 | 0.0 ± 0.0 | 8.9 ± 0.2[e] |
| 20:3(8,11,14) | 1.2 ± 0.1 | 0.7 ± 0.1[f] | 1.9 ± 0.2[e] | 1.3 ± 0.0[g] |
| 20:4(5,8,11,14) | 13.6 ± 1.2[e] | 2.8 ± 0.2 | 4.9 ± 0.4 | 3.4 ± 0.3 |
| 20:4(S,11,14,17) | 0.0 ± 0.0 | 0.0 ± 0.0 | 0.0 ± 0.0 | 1.6 ± 0.1[e] |
| 20:5(5,8,11,14,17) | 0.0 ± 0.0 | 6.9 ± 1.5[e] | 3.4 ± 0.3[e] | 1.5 ± 0.2[h] |
| 22:6(4,7,10,13,16,19) | 0.9 ± 0.1[e] | 9.7 ± 2.2[e] | 7.0 ± 0.5 | 6.0 ± 0.9 |
| Others[i] | 5.2 ± 0.9 | 4.5 ± 2.0 | 4.0 ± 0.3 | 3.4 ± 0.4 |

Notes:
[a] Each value in this table is the mean of four determinations. The value "0.0" denotes a level below the detection limit, which was 0.01%.
[b] "NMIFA": Non-methylene-interrupted fatty acid.
[c] Different from the other entries in the same row by a statistically significant degree; p < 0.05 by Fisher's Protected Least Significant Difference.
[d] Different from the safflower oil and *P. orientalis* oil entries in the same row by a statistically significant degree; p < 0.05.
[e] Different from the safflower/fish oil and *P. orientalis* oil entries in the same row by a statistically significant degree; p < 0.05.
[f] Different from the control oil and *P. orientalis* oil entries in the same row by a statistically significant degree; p < 0.05.
[g] Different from the safflower/fish oil and control oil entries in the same row by a statistically significant degree; p < 0.05.
[h] Different from the *P. orientalis* oil entry in the same row by a statistically significant degree; p < 0.05.
[i] "Others" include 16:1(9), 20:0, 20:1(11), 20:2(11,14), 20:3(8,11,14), 22:0, 22:1(13), and 24:0.

Notes:

[a] Each value in this table is the mean of four determinations. The value "0.0" denotes a level below the detection limit, which was 0.01%.

($^b$) "NMIFA": Non-methylene-interrupted fatty acid.

($^c$) Different from the other entries in the same row by a statistically significant degree; $p<0.05$ by Fisher's Protected Least Significant Difference.

($^d$) Different from the safflower oil and *P. orientalis* oil entries in the same row by a statistically significant degree; $p<0.05$.

($^e$) Different from the safflower/fish oil and *P. orientalis* oil entries in the same row by a statistically significant degree; $p<0.05$.

($^f$) Different from the control oil and *P. orientalis* oil entries in the same row by a statistically significant degree; $p<0.05$.

($^g$) Different from the safflower/fish oil and control oil entries in the same row by a statistically significant degree; $p<0.05$.

($^h$) Different from the *P. orientalis* oil entry in the same row by a statistically significant degree; $p<0.05$.

($^i$) "Others" include 16:1(9), 20:0, 20:1(11), 20:2(11,14), 20:3(8,11,14), 22:0, 22:1(13), and 24:0.

($^d$) Different from the safflower oil and *P. orientalis* oil entries in the same row by a statistically significant degree; $p<0.05$.

($^e$) Different from the safflower/fish oil and *P. orientalis* oil entries in the same row by a statistically significant degree; $p<0.05$.

($^f$) Different from the control oil and *P. orientalis* oil entries in the same row by a statistically significant degree; $p<0.05$.

($^g$) Different from the safflower/fish oil and control oil entries in the same row by a statistically significant degree; $p<0.05$.

($^h$) "Others" include 16:1(9), 20:0, 20:1(11), 20:2(11,14), 20:3(8,11,14), 22:0, 22:1(13), 24:0, and 24:1(15).

These tables show that safflower oil feeding led to a significant accumulation of 20:4 in serum phospholipids (Table IV) and serum cholesterol esters (Table V). The tables also show that the replacement of 90% of the safflower oil with fish oil resulted in predictable changes in both the serum phospholipids and the serum cholesterol esters—in both cases, both the n-6 fatty acids 18:2(9,12) and 20:4(5,

TABLE V

Further Test Results on 8-Month-Old NZB Mice
Fatty Acid Content of Total Serum Cholesterol Esters vs. Diet

| Fatty Acid ("** ... **" denotes NMIFA$^{(b)}$) | Percents of Fatty Acids Detected in Serum Cholesterol Esters (mole %)$^{(a)}$ Test Oil in Diet: | | | |
|---|---|---|---|---|
| | Safflower | Fish + Safflower (9:1) | *P. orientalis* control | *P. orientalis* |
| 16:0 | 2.6 ± 0.4 | 4.7 ± 0.3$^{(c)}$ | 2.4 ± 0.2 | 3.0 ± 0.1 |
| 18:0 | 0.3 ± 0.1 | 0.7 ± 0.2$^{(d)}$ | 0.4 ± 0.1 | 0.3 ± 0.1 |
| 18:1(9)+(11) | 4.9 ± 0.5$^{(a)}$ | 5.8 ± 0.4 | 6.8 ± 0.5 | 5.7 ± 0.0 |
| 18:2(9,12) | 35.7 ± 2.4 | 17.5 ± 0.6$^{(c)}$ | 35.5 ± 2.6 | 34.8 ± 0.7 |
| 18:3(6,9,12) | 1.0 ± 0.2$^{(c)}$ | 0.3 ± 0.1 | 0.3 ± 0.0 | 0.3 ± 0.0 |
| 18:3(9,12,15) | 0.0 ± 0.0 | 0.0 ± 0.0$^{(f)}$ | 4.4 ± 0.8 | 4.4 ± 0.3 |
| 20:3(5,11,14) | 0.0 ± 0.0 | 0.0 ± 0.0 | 0.0 ± 0.0 | 8.1 ± 0.3$^{(g)}$ |
| 20:3(8,11,14) | 0.7 ± 0.1 | 0.7 ± 0.1 | 1.1 ± 0.1$^{(g)}$ | 1.0 ± 0.1 |
| 20:4(5,8,11,14) | 51.5 ± 3.1$^{(c)}$ | 12.7 ± 0.3 | 16.4 ± 1.4 | 16.1 ± 0.8 |
| 20:4(5,11,14,17) | 0.0 ± 0.0 | 0.0 ± 0.0 | 0.0 ± 0.0 | 2.4 ± 0.1$^{(c)}$ |
| 20:5(5,8,11,14,17) | 0.0 ± 0.0$^{(c)}$ | 40.0 ± 2.0$^{(c)}$ | 23.3 ± 1.6$^{(c)}$ | 12.8± 0.7$^{(c)}$ |
| 22:6(4,7,10,13,16,19) | 0.4 ± 0.2$^{(c)}$ | 9.4 ± 0.5 | 6.1 ± 0.5$^{(c)}$ | 8.7 ± 0.2 |
| Others$^{(h)}$ | 2.9 ± 1.0 | 5.5 ± 1.1$^{(c)}$ | 2.3 ± 0.6 | 1.9 ± 0.2 |

Notes:
$^{(a)}$Each value in this table is the mean of four determinations. The value "0.0" denotes a level below the detection limit, which was 0.01%.
$^{(b)}$"NMIFA": Non-methylene-interrupted fatty acid.
$^{(c)}$Different from the other entries in the same row by a statistically significant degree; $p < 0.05$ by Fisher's Protected Least Significant Difference.
$^{(d)}$Different from the safflower oil and *P. orientalis* oil entries in the same row by a statistically significant degree; $p < 0.05$.
$^{(e)}$Different from the safflower/fish oil and *P. orientalis* oil entries in the same row by a statistically significant degree; $p < 0.05$.
$^{(f)}$Different from the control oil and *P. orientalis* oil entries in the same row by a statistically significant degree; $p < 0.05$.
$^{(g)}$Different from the safflower/fish oil and control oil entries in the same row by a statistically significant degree; $p < 0.05$.
$^{(h)}$"Others" include 16:1(9), 20:0, 20:1(11), 20:2(11,14), 20:3(8,11,14), 22:0, 22:1(13), 24:0, and 24:1(15).

Notes:

($^a$) Each value in this table is the mean of four determinations. The value "0.0" denotes a level below the detection limit, which was 0.01%.

($^b$) "NMIFA": Non-methylene-interrupted fatty acid.

9$^c$) Different from the other entries in the same row by a statistically significant degree; $p<0.05$ by Fisher's Protected Least Significant Difference.

8,11,14) were replaced by n-3 fatty acids 20:5(5,8,11,14,17) and 22:6(4,7,10,13,16,19). The control diet, which is rich in the n-3 fatty acid 18:3(9,12,15), also reduced the levels of the n-6 fatty acid 20:4(5,8,11,14) (arachidonic acid) in both phospholipids and cholesterol esters with parallel increases in the n-3 fatty acids 20:5(5,8,11,14,17) and 22:6(4,7,10,13, 16,19). Thus, 18:3 is an effective dietary component in the modulation of serum 20:4.

The most striking result was the conspicuous accumulation of the NMIFA 20:3(5,11,14) in the serum phospholipids of mice fed *P. orientalis* oil (Table IV). In spite of the fact that it constitutes only a minor fraction (3.1%, Table III) of the *P. orientalis* oil which these mice were fed, it was the major 20-carbon fatty acid in serum phospholipids in all mice that were fed the *P. orientalis* oil. This establishes that the NMIFA 20:3(5,11,14) served as a potent modulator of serum phospholipids.

In contrast to its detected level in phospholipids and cholesterol esters, the NMIFA 20:3(5,11,14) was not detected in serum triglycerides.

EXAMPLE 3

Study of Incorporation of NMIFA's Into Membrane Lipids

When the mice had reached the age of sixteen months, the mice were sacrificed and samples of hepatic and spleen tissue were obtained. Lipids were extracted from the tissue samples by the procedure described in Example 2 above. In the identification of phospholipids as a class subsequent to the HPTLC, the phospholipid class was further broken down into phosphatidyl cholines, phosphatidyl ethanolamines and phosphatidyl inositols. The final results in terms of individual fatty acid contents of these lipid classes in the hepatic tissue for each dietary group of the mice are shown in Tables VI (phosphatidyl cholines), VII (phosphatidyl ethanolamines) and VIII (phosphatidyl inositols). The data from the spleen tissue samples is not shown in these tables.

TABLE VI

Test Results on 16-Month-Old Mice Fatty Acid Content of Phosphatidyl Chorine in Hepatic Membrane vs. Diet

| | Percents of Fatty Acid in Hepatic Phosphatidyl Chorine (mole %) Test Oil in Diet: | | | |
|---|---|---|---|---|
| Fatty Acid ("** ... **" denotes NMIFA[a]) | Saf- flower | Fish + Safflower (9:1) | P. orientalis control | P. orientalis |
| 16:0 | 26.9 | 36.8 | 30.2 | 30.6 |
| 18:0 | 24.9 | 17.5 | 19.6 | 16.0 |
| 18:1(9) | 6.5 | 9.3 | 11.4 | 8.7 |
| 18:2(9,12) | 19.2 | 10.6 | 15.4 | 15.7 |
| 20:3(8,11,14) | 0.4 | 0.7 | 1.1 | 0.9 |
| 20:4(5,8,11,14) | 15.5 | 3.9 | 8.1 | 7.1 |
| 22:4(7,10,13,16) | 0.6 | 0.0 | 0.0 | 0.0 |
| 22:5(4,7,10,13,16) | 3.9 | 0.0 | 0.0 | 0.0 |
| 20:5(5,8,11,14,17) | 0.0 | 3.5 | 2.5 | 1.4 |
| 22:5(7,10,13,16,19) | 0.0 | 1.0 | 0.5 | 1.0 |
| 22:6(4,7,10,13,16,19) | 0.8 | 15.4 | 9.1 | 14.3 |
| 20:3(5,11,14) | 0.0 | 0.0 | 0.0 | 2.2 |
| 20:4(5,11,14,17) | 0.0 | 0.0 | 0.0 | 0.1 |
| Others | 1.1 | 1.3 | 1.1 | 1.0 |

[a]"NMIFA": Non-methylene-interrupted fatty acid.

TABLE VIII

Further Test Results on 16-Month-Old Mice Fatty Acid Content of Phosphatidyl Ethanolamine in Hepatic Membrane vs. Diet

| | Percents of Fatty Acid in Hepatic Phosphatidyl Ethanolamine (mole %) Test Oil Included in Diet: | | | |
|---|---|---|---|---|
| Fatty Acid ("** ... **" denotes NMIFA[a]) | Saf- flower | Fish + Safflower (9:1) | P. orientalis control | P. orientalis |
| 16:0 | 20.5 | 25.6 | 20.5 | 20.4 |

TABLE VIII-continued

Further Test Results on 16-Month-Old Mice Fatty Acid Content of Phosphatidyl Ethanolamine in Hepatic Membrane vs. Diet

| | Percents of Fatty Acid in Hepatic Phosphatidyl Ethanolamine (mole %) Test Oil Included in Diet: | | | |
|---|---|---|---|---|
| Fatty Acid ("** ... **" denotes NMIFA[a]) | Saf- flower | Fish + Safflower (9:1) | P. orientalis control | P. orientalis |
| 18:0 | 31.2 | 27.5 | 24.9 | 21.7 |
| 18:1(9) | 6.4 | 3.7 | 9.5 | 6.7 |
| 18:2(9,12) | 6.3 | 2.2 | 4.0 | 4.2 |
| 20:3(8,11,14) | 0.1 | 0.8 | 0.5 | 0.4 |
| 20:4(5,8,11,14) | 16.9 | 3.9 | 10.4 | 9.7 |
| 22:4(7,10,13,16) | 2.2 | 0.0 | 0.0 | 0.1 |
| 22:5(4,7,10,13,16) | 12.9 | 0.0 | 0.0 | 0.0 |
| 20:5(5,8,11,14,17) | 0.0 | 3.8 | 3.7 | 2.1 |
| 22:5(7,10,13,16,19) | 0.0 | 1.7 | 1.6 | 1.8 |
| 22:6(4,7,10,13,16,19) | 3.0 | 30.1 | 23.9 | 30.5 |
| 20:3(5,11,14) | 0.0 | 0.0 | 0.0 | 1.4 |
| 20:4(5,11,14,17) | 0.0 | 0.0 | 0.0 | 0.1 |
| Others | 0.5 | 0.5 | 0.4 | 0.4 |

[a]"NMIFA": Non-methylene-interrupted fatty acid.

TABLE VIII

Further Test Results on 16-Month-Old Mice Fatty Acid Content of Phosphatidyl Inositol in Hepatic Membrane vs. Diet

| | Percents of Fatty Acid in Hepatic Phosphatidyl Inositol (mole %) Test Oil Included in Diet: | | | |
|---|---|---|---|---|
| Fatty Acid ("** ... **" denotes NMIFA[a]) | Saf- flower | Fish + Safflower (9:1) | P. orientalis control | P. orientalis |
| 16:0 | 4.6 | 7.2 | 4.8 | 5.6 |
| 18:0 | 61.1 | 53.8 | 55.9 | 53.4 |
| 18:1(9) | 2.0 | 1.2 | 2.1 | 1.8 |
| 18:2(9,12) | 1.3 | 0.7 | 1.0 | 1.3 |
| 20:3(8,11,14) | 0.4 | 0.3 | 0.6 | 0.8 |
| 20:4(5,8,11,14) | 30.4 | 28.2 | 29.9 | 28.3 |
| 22:4(7,10,13,16) | 0.0 | 0.0 | 0.0 | 0.0 |
| 22:5(4,7,10,13,16) | 0.0 | 0.0 | 0.0 | 0.0 |
| 20:5(5,8,11,14,17) | 0.0 | 2.9 | 1.17 | 0.6 |
| 22:5(7,10,13,16,19) | 0.0 | 1.8 | 1.2 | 1.0 |
| 22:6(4,7,10,13,16,19) | 0.6 | 2.4 | 0.9 | 1.2 |
| 20:3(5,11,14) | 0.0 | 0.0 | 0.0 | 5.8 |
| 20:4(5,11,14,17) | 0.0 | 0.0 | 0.0 | 0.1 |
| Others | 1.1 | 0.9 | 1.4 | 1.2 |

[a]"NMIFA": Non-methylene-interrupted fatty acid.

Tables VI and VII show that safflower oil feeding led to a significant accumulation of 20:4 in the tissue phosphatidyl cholines and phosphatidyl ethanolamines. These results are consistent with results obtained for shorter feeding periods, as reported in the literature (Berger, A., et al., *Biochem. Biophys. Acta* 1085:371–376 (1991); Berger, A., et al., *Nutritional Biochemistry* 4(7):409–420 (1993)). Also, as it did in the serum studies, the replacement of 90% of the safflower oil with fish oil resulted in the replacement of the n-6 fatty acids 18:2(9,12) and 20:4(5,8,11,14) with the n-3 fatty acids 20:5(5,8,11,14,17) and 22:6(4,7,10,13,16,19). In further similarity to the results from the serum studies, the control diet, which is rich in the n-3 fatty acid 18:3(9,12,15), reduced the levels of the n-6 fatty acid 20:4(5,8,11,14) with parallel increases in the n-3 fatty acids 20:5(5,8,11,14,17) and 22:6(4,7,10,13,16,19), although the degree to which arachidonic acid 20:4(5,8,11,14) was replaced by 20:5(5,8,11,14,17) and 22:6(4,7,10,13,16,19) was not as great.

The NMIFA's 20:3(5,11,14) and 20:4(5,11,14,17) were incorporated into membrane phospholipids to varying extents depending on the fatty acid, the tissue and the phospholipid class. The NMIFA 20:4(5,11,14,17) (n-3) was not incorporated into any membrane above 0.1%, and thus was virtually absent from all membranes examined. Although replacement of the arachidonic acid by the NMIFA 20:3(5,11,14) was not as dramatic in hepatic and spleen membranes as in plasma phospholipids, significant replacement nevertheless occurred. Furthermore, the esterification of the NMIFA 20:3(5,11,14) into the phosphatidyl inositol lipid class was significantly more efficient than the esterification of both n-6 and n-3 methylene-interrupted fatty acids. It may also be noted that the accumulation of this NMIFA in the phosphatidyl inositol class (Table VIII) was greater than its accumulation in all other classes (Tables VI and VII).

It is also significant to note that the levels of the n-3 fatty acid 22:6(4,7,10,13,16,19), which is the alesaturation product of 18:3(9,12,15), in the *P. orientalis* dietary group, were equal to or greater than the levels of the same fatty acid in the *P. orientalis* control dietary group. Since the diets of both groups contained equal amounts of 18:3(9,12,15), this leads to the conclusion that the mechanism of the replacement of the arachidonic acid by the NMIFA is one involving competition for the incorporation and reacylation rather than one involving inhibition of fatty acid desaturation.

EXAMPLE 4

Study of Effect on Onset of Anti-Erythrocyte Autoantibodies

Direct Coombs' tests were performed on each of the four dietary groups of the mice, according to art-recognized procedures as reported by Chiang, B.-L., *et al.*, *J. Immunol.* 145:94–101 (1990), at one-month intervals beginning at seven months of age. The procedure involved collecting blood retro-orbitally into heparinized capillary tubes and washing the cells three times with phosphate-buffered saline (PBS). Packed cells in amounts of 25μL were added to 1 mL of PBS with 1% bovine serum albumin. Two-fold serial dilutions of antimouse polyvalent immunoglobulin (M8019, Sigma Chemical Co., St. Louis, Mo., U.S.A.) were established in round-bottom microtiter plates, with a total volume of antisera per well of 25 mL. Each well was then charged with 25 μL of red cell suspension, and the well contents were mixed. Agglutination was determined after a 4-hour incubation at room temperature. The data were presented as the amount of direct antiglobulin titer as the function of log 2. Known positive and negative controls were used.

Figure 2:
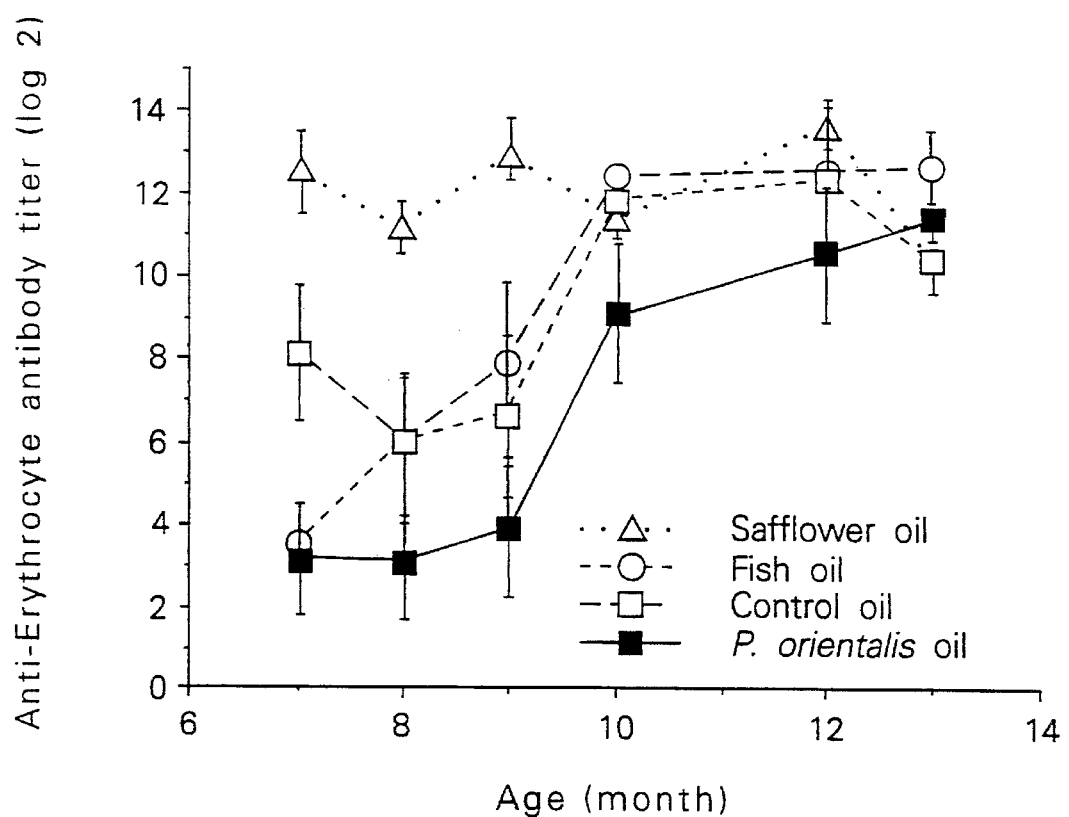
FIG. 2 is a representation of experimental results in which the appearance of antierythrocyte antibodies is correlated to the presence of NMIFA's in the diet.

The results are plotted in FIG. 2, where the triangles represent mice from the safflower oil dietary group, the circles the fish/safflower oil dietary group, the open squares the *P. orientalis* control group, and the filled squares the *P. orientalis* group.

Differences among the plotted data were considered statistically significant when p<0.05, according to Fisher's Protected l2,Least Significant Difference, referenced above. Such differences were noted as follows:

at seven months: safflower oil vs. fish/safflower and *P. orientalis* oils;
P. orientaliscontrol oil vs. fish/safflower and *P. orientalis* oil at eight months: safflower oil vs. fish/safflower and *P. orientalis* oils at nine months: safflower oil vs. fish/safflower and *P. orientalis* control and *P. orientalis* oils at ten months: safflower oil vs. *P. orientalis* oil The results can be summarized as follows. Although mice fed either *P. orientalis* oil or fish/safflower oil had a slower onset of anti-erythrocyte autoantibodies than the control or safflower oil groups, the mice fed *P. orientalis* oil had the lowest levels overall of autoantibody titers. From seven to ten months of age, mice fed *P. orientalis* oil showed statistically lower autoantibody titers than those fed the safflower oil. At seven months of age, the autoantibody liters of mice fed *P. orientalis* oil were also less than those of the [<m]ditP. orientalis oil control group. Similarly, the autoantibody titers of the mice fed fish oil were statistically lower than those of the safflower mice until nine months of age. At seven months of age, the fish oil group also had lower autoantibody titers than the control oil mice. Comparison of *P. orientalis* and fish oil mice indicates that from seven to twelve months of age, the autoantibody timrs of the *P. orientalis* oil mice were statistically lower.

Overall, the *P. orientalis* oil was the most effective in delaying the onset of antierythrocyte autoantibodies amont NZB mice.

Figure 3:
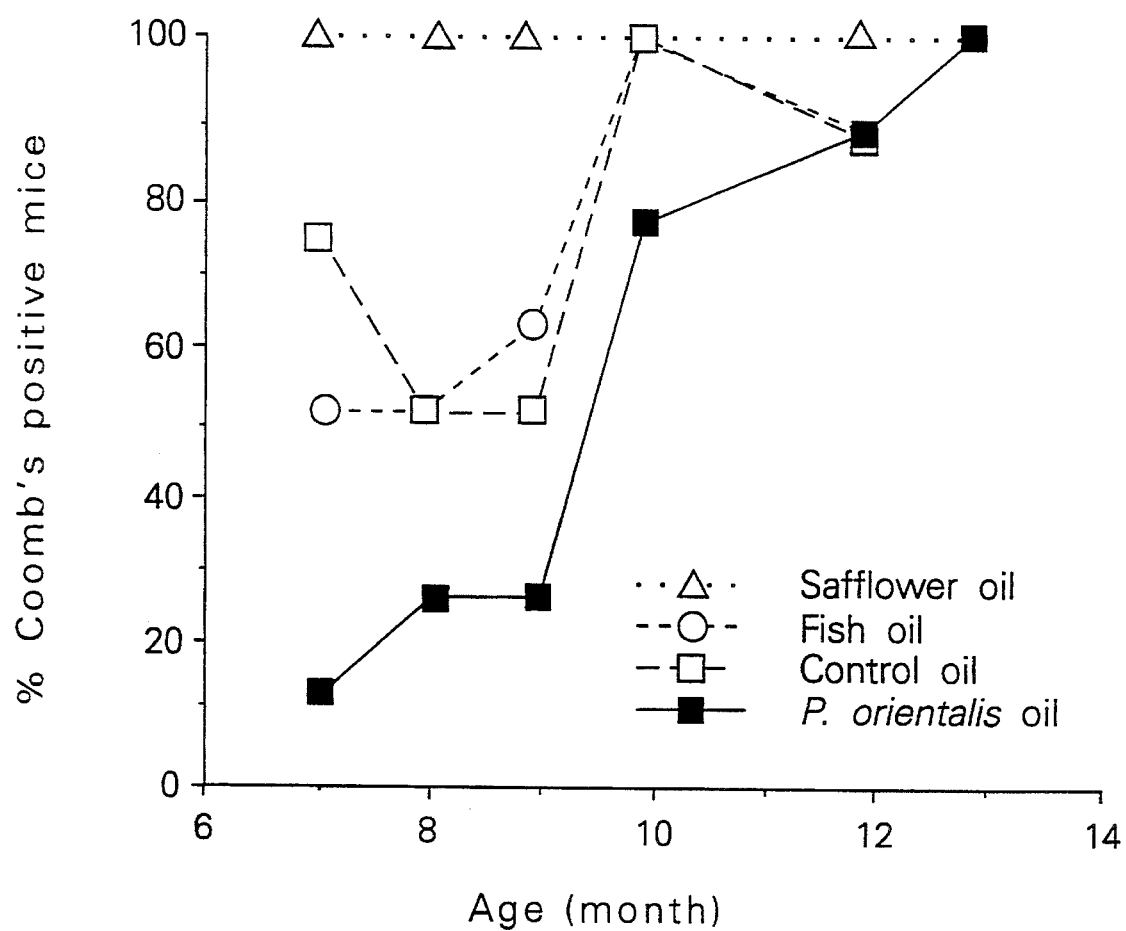
FIG. 3 is a further representation of results from the experiment represented in FIG. 2.

Individual mice with titers (log 2) of autoantibodies equal to or greater than 4 were judged to be Coombs' positive, based on comparisons to data obtained from the sera of normal mice. Coombs' positivity was determined for eight mice in each dietary group, and the results in terms of the percentage of the group which were positive according to this criterion are plotted in FIG. 3, where the groups are distinguished by the same notations used in FIG. 2. Statistically significant differences, according to Fisher's Exact Test (p<0.05), were noted as follows:

at seven months: safflower oil vs. fish/safflower oil; *P. orientalis* control oil vs. *P. orientalis* oil; safflower oil vs. *P. orientalis* oil at eight months: safflower oil vs. fish/safflower oil; safflower oil vs. *P. orientalis* control oil; safflower oil vs. *P. orientalis* oil at nine months: safflower oil vs. *P. orientalis* control oil; safflower oil vs. *P. orientalis* oil The results may be summarized as follows. All safflower oil-fed mice were Coombs' positive by seven months of age while fish oil-fed mice attained 50% positivity. Seventy-five percent of the mice fed *P. orientalis* control oil were Coombs' positive, as opposed to only 12% of the mice fed *P. orientalis* oil. Both fish oil and *P. orientalis* control oil groups achieved 100% incidence by ten months of age; *P. orientalis* oil, by contrast, had a frequency of only 75%. By thirteen months of age, 100% of the mice fed *P. orientalis* oil were positive, but this group was the last group to become so.

The foregoing is offered primarily for purposes of illustration. It will be readily apparent to those skilled in the art that the formulations, methods of administration and other parameters of the invention described herein may be further modified or substituted in various ways without departing from the spirit and scope of the invention.

What is claimed is:

1. A method of suppressing autoimmune disease in a mammalian subject suffering therefrom, said method comprising administering to said subject a therapeutically effective amount of a compound having the formula

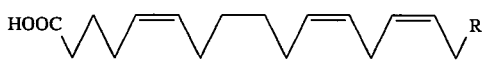

in which R is a member selected from the group consisting of $C_1$–$C_{10}$ alkl, $C_2$–$C_{10}$ alk-1-enyl, $C_2$–$C_{10}$ alka-1,4-dienyl, and $C_2$–$C_{10}$ alka-1,4,7-trienyl.

2. A method in accordance with claim 1 in which R is a member selected from the group consisting of $C_1$–$C_6$ alkyl and $C_2$–$C_6$ alk-1-enyl.

3. A method in accordance with claim 2 in which R is 1-n-butenyl.

4. A method in accordance with claim 2 in which R is 1-n-butyl.

5. A method in accordance with claim 1 comprising administering said compound to said subject orally.

6. A method in accordance with claim 1 comprising administering said compound by enteral infusion.

* * * * *

UNITED STATES PATENT AND TRADEMARK OFFICE
CERTIFICATE OF CORRECTION

PATENT NO. : 5,456,912

DATED : October 10, 1995

INVENTOR(S) : J. Bruce German, M. Eric Gershwin and Alvin Berger

It is certified that error appears in the above-indentified patent and that said Letters Patent is hereby corrected as shown below:

Column 1, line 64, delete "en" and insert --enyl,--

Column 4, line 4, delete "lameliar" and insert --lamellar--

Column 4, line 41, delete "ironspecific" and insert --iron-specific--

Column 7, line 15, delete "I." and insert --J.--

Column 8, Table IV, delete "20:4(S,11,14,17)" and insert --20:4(5,11,14,17)--

Column 9, Notes: delete "9°)" and insert --(°)--

Column 13, line 57, delete "I2,"

Column 13, line 61, after oils; insert --*P. orientalis* control oil vs. fish/safflower and *P. orientalis* oil--

Column 13, delete line 62 and 63;

UNITED STATES PATENT AND TRADEMARK OFFICE
CERTIFICATE OF CORRECTION

PATENT NO. : 5,456,912

DATED : October 10, 1995

INVENTOR(S) : J. Bruce German, M. Eric Gershwin and Alvin Berger

It is certified that error appears in the above-indentified patent and that said Letters Patent is hereby corrected as shown below:

Column 14, line 10, delete "liters" and insert --titers--

Column 14, line 12, delete "[≤m]dit"

Column 14, line 19, delete "timrs" and insert --titers--

Column 14, line 22, delete "antierythrocyte" and insert --anti-erythrocyte--

Column 15, line 6, delete "alkl" and insert --alkyl--

Column 16, line 4, delete "1-"

Signed and Sealed this

Second Day of April, 1996

Attest:

BRUCE LEHMAN

Attesting Officer         Commissioner of Patents and Trademarks